United States Patent [19]
Fogel et al.

[11] 4,227,876
[45] Oct. 14, 1980

[54] ORTHODONTIC BRACKET

[76] Inventors: Maxwell S. Fogel, Apt. 1801, 9100 Atlantic Ave., Island House; Jack M. Magill, Apt. 1010, 9600 Condominium, 9600 Atlantic Ave., both of Margate, N.J. 08402

[21] Appl. No.: 12,622

[22] Filed: Feb. 16, 1979

[51] Int. Cl.³ .............................................. A61C 3/00
[52] U.S. Cl. ................................................... 433/11
[58] Field of Search .................... 32/14 A; 433/10, 11

[56] References Cited
U.S. PATENT DOCUMENTS

| | | | |
|---|---|---|---|
| 2,265,420 | 12/1941 | Brusse et al. | 32/14 A |
| 2,915,824 | 12/1959 | Kesliny | 433/11 |
| 3,164,901 | 1/1965 | Wallshein | 32/14 A |
| 3,178,822 | 4/1965 | Fogel et al. | 32/14 A |
| 3,327,393 | 6/1967 | Brader | 433/11 |

*Primary Examiner*—Robert Peshock
*Attorney, Agent, or Firm*—Caesar, Rivise, Bernstein & Cohen, Ltd.

[57] ABSTRACT

An orthodontic bracket is provided which comprises a pair of spaced apart arch wire securement members, each having an opening with a flared mouth. The members are secured at opposite ends of a base which base is securable to the anterior surface of a tooth. An auxiliary bracket is secured to the base between the members which bracket includes a slot that extends in a straight line which traverses the openings of the members. The auxiliary bracket includes a vertically extending channel for receipt of an insert bracket which has an enlarged head which is in the shape of said spaced apart members. Said spaced apart members and said enlarged head include an opening with a flared mouth to enable self-locking of an arch wire in the openings of said members.

7 Claims, 10 Drawing Figures

ORTHODONTIC BRACKET

This invention relates generally to orthodontic brackets and more particularly to an orthodontic bracket which facilitates securement of an arch wire in the brackets and eliminates ligature tying.

Prior to the conception of the instant invention, the inventors herein designed what is known in the field of orthodontics as the Fogel-Magill Edgewise Combination Bracket. The bracket is secured to the tooth either by welding to a backing or to a band which fits over a tooth. The bracket is therefore secured by the band or backing on the anterior surface of the tooth. The bracket includes a pair of auxiliary edgewise brackets, each of which includes a horizontally disposed slot of a rectangular cross-section and on the band side of the bracket (the side adjacent to the tooth) a vertical slot is provided for receipt of an insert bracket.

The prior art bracket permits three stages of treatment of the patient. In the first stage, the insert bracket is inserted into the vertical slot in the edgewise bracket and secured therein by bending the bracket appropriately. A lightwire is inserted into the head of the insert bracket and is snapped into the head of the insert bracket, which includes an opening having a flared mouth which permits the round cross-section lightwire to be snapped into the opening through the mouth of the enlarged head of the insert bracket.

A clamping tool is then used to deform the head of the insert bracket so that the arch wire is secured into the opening of the insert bracket.

In the second stage of treatment of the orthodontic patient, the insert bracket is removed from each of the brackets in the mouth and an arch wire is then placed in the slot which extends horizontally through the bracket. Each of the auxiliary brackets include a pair of outwardly extending flanges which extend in opposed directions from the slot and which flanges are used for ligature tying after the arch wire is located within the horizontally disposed slot. In order to secure the arch wire within the pair of auxiliary brackets in each of the brackets, a ligature wire is secured about each auxiliary bracket to attach the arch wire at two points within the combination bracket.

In a third stage of treatment, in place of a round cross-section arch wire an arch wire of rectangular cross-section is fit into the horizontal slot and is tied in the same manner as the round cross-section arch wire to the bracket.

In both the second and third stages of treatment the arch wire which is tied with ligatures to the auxiliary brackets must be done by a skilled technician or orthodontist because it requires great skill to tie the arch wire in place with the tiny auxiliary brackets that are used to hold the wire in place.

Considerable training must be given to technicians or orthodontists and, unless great manual dexterity is possessed by the technician or orthodontist, ligature tying is not only time consuming, but extremely difficult.

It is therefore an object of this invention to overcome the aforementioned disadvantages of the prior art bracket.

Another object of the invention is to provide a new and improved orthodontic bracket which includes a self-locking mechanism for edgewise securement of arch wires.

Another object of the invention is to provide a new and improved orthodontic bracket which can be used as flexibly as the prior art brackets, but which obviates the need for expensive and time consuming ligature tying.

Still another object of this invention is to provide a new and improved orthodontic bracket which facilitates securement of an arch wire, yet provides reduced frictional relationship in both the lightwire and edgewise phases of treatment.

These and other objects of the invention are achieved by providing an orthodontic bracket which comprises a pair of spaced apart arch wire securement members, each having an opening with a flared mouth. An intermediate member is provided having a slot that extends in a straight line which traverses the openings of the members. The intermediate member has a vertically extending channel for receipt of a removable insert bracket having an enlarged head which includes an opening with a flared mouth.

Other objects and many of the attendant advantages of this invention will be readily appreciated as the same becomes better understood by reference to the following detailed description when considered in connection with the accompanying drawing wherein.

Referring now in greater detail to the various figures of the drawing wherein like reference numerals refer to like parts, an orthodontic bracket embodying the invention is shown generally at 20 in FIG. 1.

Figure 1:
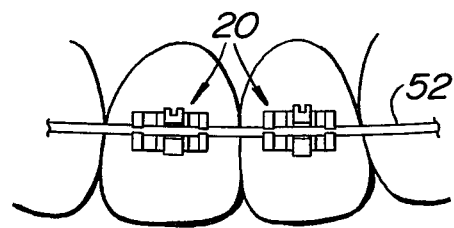
FIG. 1 is a front elevational view of a plurality of orthodontic brackets embodying the invention, securing an arch wire in place.

Each of the brackets shown in FIG. 1 are shown attached to the anterior surface of a tooth by a bonding agent, or a suitable adhesive. The bracket 20 may also be secured to the anterior surface of a tooth by welding the bracket to a band which is secured about the tooth by a suitable dental cement.

Figure 2:
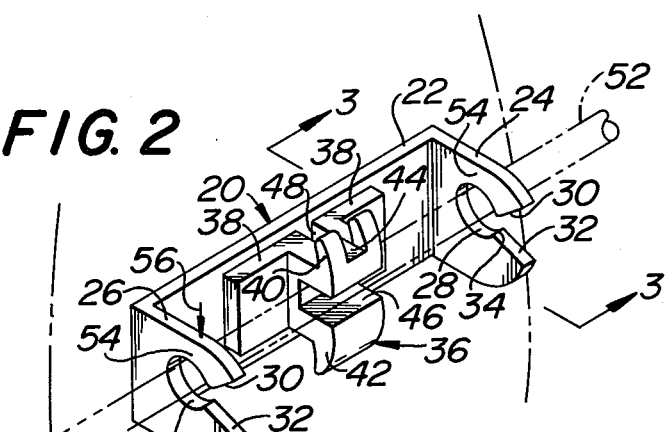
FIG. 2 is an enlarged perspective view of an orthodontic bracket embodying the invention.

Referring to FIG. 2 it can be seen that the bracket 20 basically comprises a U-shaped stainless steel member having a base 22 and a pair of securement members 24 and 26 which are attached to the base integrally at each end thereof so that the securement members 24 and 26 are spaced apart by the length of the base 22. The base 22 is a rectangular flat member which generally conforms in shape to the outer surface of the tooth to which the bracket is secured. The surface of base 22 which faces the tooth is secured to the tooth by using a mesh backing which is secured to the tooth by an adhesive. The base is then welded to the backing. The bracket may also be secured by welding to a band which is secured to the tooth by means of a dental cement.

Figure 3:
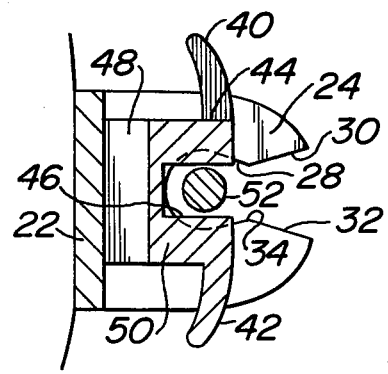
FIG. 3 is an enlarged cross-sectional view taken along the line 3—3 in FIG. 2.

Each of the securement members 24 and 26 is generally C-shaped and includes an opening 28 which is of circular cross-section. As best seen in FIG. 3 opening 28 includes an entry mouth which is formed by the edges 30 and 32 of the C-shaped securement member 24. The edges 30 and 32 of the C-shaped securement member form a flared mouth for opening 28 which is widest at the outermost portion of member 24 and narrowest at the junction 34 between the mouth and the opening.

An auxiliary bracket 36 is secured to the anterior surface of base 22 between the securement members 24 and 26. The auxiliary bracket 36 includes a pair of L-shaped base portions 38. The L-shaped base portions 38 are suitably secured by welding to the front surface of the base 22. At the end of each leg of the L-shaped member which extends outwardly of the base 22 is an upwardly extending flange 40 and a downwardly extending flange 42. Flange 40 is slotted at 44 which, as will hereinafter be seen, accomodates an insert bracket and flange 42 extends downwardly in the direction opposed from flange 40. The flanges 40 and 42 are spaced by a horizontally extending slot 46 which is of rectangular cross-section. The slot 46 extends in a line with the openings 28 of the securement members 24 and 26. The auxiliary bracket 36 also includes a vertical slot which is between the base 22 and the U-shaped member 50 which supports the flanges 40 and 42.

As seen in FIGS. 1 and 2 an arch wire 52 is seen extending through the openings 28 in the bracket 20. In order to insert the arch wire 52, the arch wire is urged towards the openings 28 in the mouth that is formed by edges 30 and 32 of each of the securement members 24 and 26. At the junctions 34, the space between the junctions 34 of edges 30 and 32 is slightly smaller in diameter than that of the arch wire 52 so that when the arch wire 52 is urged towards the opening it is snapped into the opening as the wire passes junction 34.

Each of the C-shaped securement members 24 and 26 includes a portion 54 of reduced thickness which is deformable so that a crimping tool can be used to secure the arch wire 52 firmly in the openings 28. That is, by using a crimping tool of a plier-like type and engaging the member 24 or 26 for the purpose of crimping by providing an inwardly disposed force in the direction of arrows 56 and 58 in FIG. 2 the edges 30 and 32 are urged together and remain in that condition to firmly secure the arch wire within opening 28. Thus, the bracket enables an arch wire to be slidably secured quickly at two spaced portions of the bracket. This enables the tooth to be engaged by the wire quickly without impeding lateral movement of the wire with respect to the tooth to which the bracket is attached. This enables controlled movement of the tooth in all directions.

Figure 4:
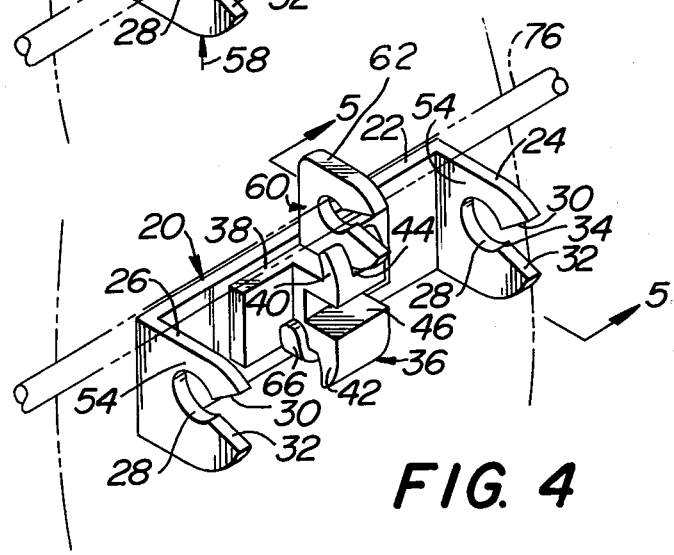
FIG. 4 is an enlarged perspective view of the orthodontic bracket embodying the invention having the insert bracket secured therein.
Figure 5:
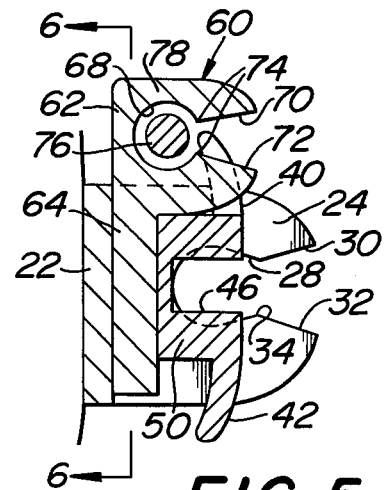
FIG. 5 is an enlarged sectional view taken along the line 5—5 in FIG. 4.
Figure 6:
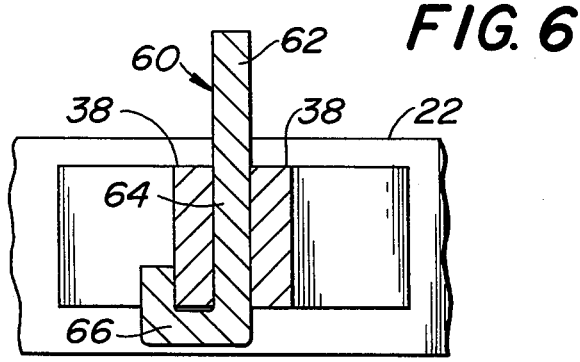
FIG. 6 is an enlarged sectional view taken along the line 6—6 in FIG. 5.

Referring now to FIG. 4, the orthodontic bracket 60 embodying the invention is shown with an insert bracket 60 secured within the vertical slot 48. As best seen in FIGS. 4 and 5, the insert bracket 60 includes an enlarged head 62 and a stem 64. The stem 64 is extended into the slot 48 and as best seen in FIG. 6 is bent about one of the L-shaped members 38 of the auxiliary bracket. Thus, at 66 the stem 64 is bent about the bottom of the L-shaped member 38. The head 62 of the insert bracket is C-shaped and acts as a securement member for a light arch wire. The head 62 of the insert bracket thus includes an opening 68 which includes a mouth comprised of edges 70 and 72.

The edges 70 and 72 join the opening 68 at junctions 74 which junctions are spaced slightly less than the diameter of arch wire 76, which is received in the opening 68. Thus, the arch wire 76 is inserted into the opening by forcing the arch wire 76 into the opening 68 past the junctions 74 and the wire is snapped in place as it passes the junctions 74. To secure the arch wire 76 within the opening 68, a crimping tool is used for deforming the smaller portion 78 of the head so that the edges 70 and 72 are urged together. As best seen in FIG. 4, the head 62 of the insert bracket fits in the slot 44 of flange 40. The insert bracket 60 thus enables a wire to be connected in a single point connection to a tooth when used as shown in FIGS. 4, 5 and 6.

Figure 8:
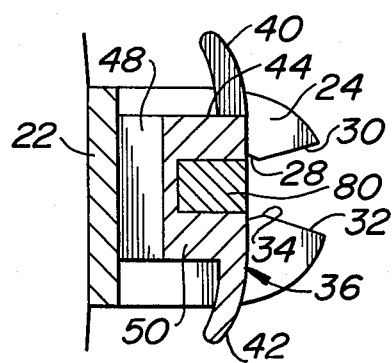
FIG. 8 is an enlarged sectional view taken along the line 8—8 in FIG. 7.
Figure 7:
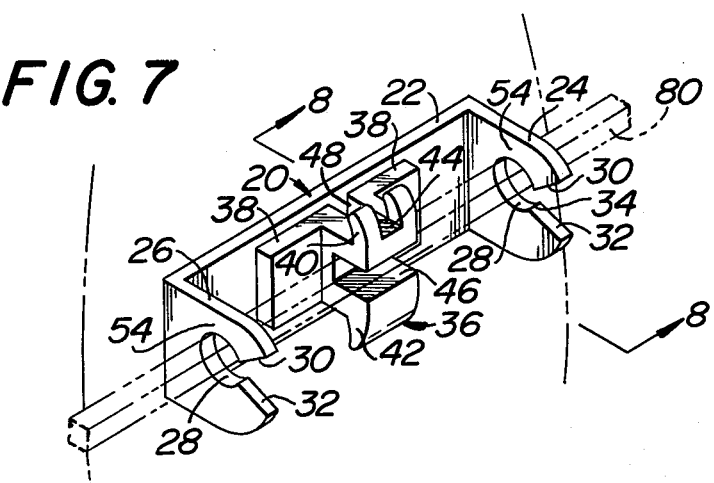
FIG. 7 is an enlarged perspective view of the orthodontic bracket embodying the invention and being used in combination with an arch wire of rectangular cross-section.

In FIG. 7, the auxiliary bracket 36 is shown in use with an arch wire of rectangular cross-section. The arch wire 80 is shown extending through the openings in securement members 24 and 26. In addition, the rectangular cross-section arch wire 80, as best seen in FIG. 8, fits snuggly within the horizontally disposed rectangular cross-sectioned slot 46 of the auxiliary bracket 36.

Figure 9:
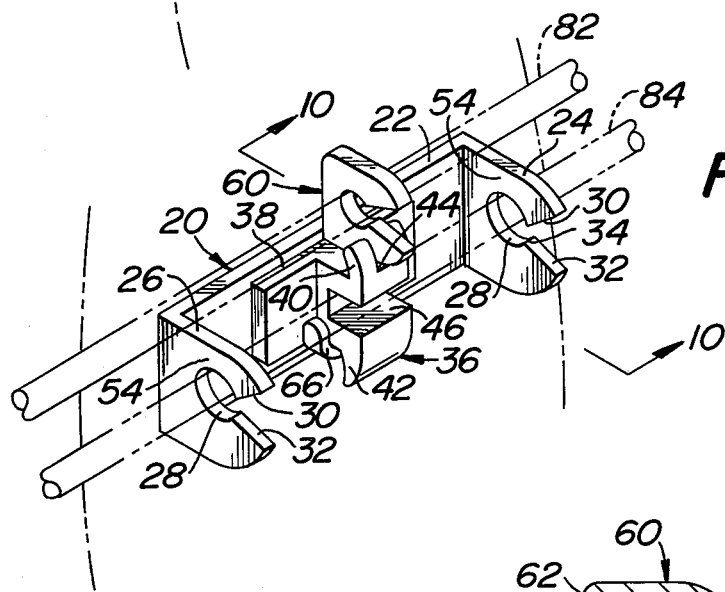
FIG. 9 is an enlarged perspective view of the bracket embodying the invention for use in combination with a pair of arch wires.

In FIG. 9 the orthodontic bracket embodying the invention is shown in use with the insert bracket 60 shown in use on the base 20 so that a pair of arch wires 82 and 84 can be simultaneously secured to the bracket.

Thus, the bracket enables a first arch wire 82 to be secured at a single point with respect to the tooth by the head 62 of the insert bracket 60. In addition, the arch wire 84 which may be round or rectangular, is secured at two points by the securement members 22 and 24 of the bracket.

It can therefore be seen that a new and improved orthodontic bracket has been provided.

The orthodontic bracket facilitates the securement of arch wires to the teeth in the four stages of orthodontic treatment specified above.

That is, in the first stage an upper wire is placed in the insert bracket head as shown in FIGS. 4 and 5. The light arch wire 76 is held as in the prior art by the use of the insert bracket 60 which can be crimped to secure the light arch wire 76.

In the second stage of orthodontic treatment a round arch wire is secured within the openings 28 of the securement members 24 and 26 of the bracket by urging the arch wire into the openings 28 of the members 24 and 26 and within slot 46 of the auxiliary bracket 36. The arch wire 52 is then maintained in place by crimping the members 24 and 26 so that the edges 30 and 32 close about the arch wire 52. Thus, the time consumption and expense of ligature tying, as well as learning the technique of tying, is obviated since only crimping of the end members 24 and 26 are required for making a two point connection with the arch wire 52.

In the third stage of treatment, an arch wire 80 of rectangular cross-section is secured in the openings of securement members 24 and 26 of the bracket with the central portion of the wire with respect to the tooth being engaged in slot 46 of the auxiliary bracket 36 as shown in FIG. 7 and FIG. 8.

Figure 10:
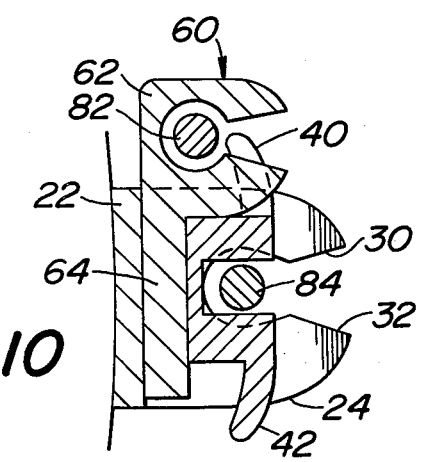
FIG. 10 is an enlarged cross-sectional view taken along the line 10—10 in FIG. 9.

Finally, in a final stage of treatment the insert bracket may be used in the slot of the auxiliary bracket as shown in FIGS. 9 and 10 so that a pair of arch wires 82 and 84 can be used simultaneously for treatment. This enables torquing the roots of anterior teeth with the arch wire in the insert bracket while holding the teeth in position with the main arch wire in the auxiliary bracket.

It should also be noted that the auxiliary bracket 36 provided in the center may also be provided with an inclined slot to facilitate torquing with a rectangular arch wire.

Finally, it should be noted that the bracket enables arch wires to be used in both one point and multi-point connections simultaneously.

Without further elaboration, the foregoing will so fully illustrate our invention that others may, by applying current or future knowledge, readily adapt the same for use under various conditions of service.

What is claimed as the invention is:

1. In combination an orthodontic bracket for securement to the anterior surface of teeth and an arch wire, said bracket including a pair of planar C-shaped spaced securement members, each of said members including a portion of reduced thickness each of said members including an opening with a flared mouth to facilitate insertion of said arch wire, said mouth being narrowest at the junction of said mouth and said opening, the diameter of said arch wire being slightly larger than the width of the smallest opening of said mouth so that said arch wires are snapped into said opening when said arch wire is urged therein, said members each being deformed in the plane of said member with said mouth closed by squeezing said members about said opening with a plier type tool so that said bracket securely holds said arch wire at two spaced apart points.

2. An orthodontic bracket for securement to the anterior surface of teeth, said bracket including a pair of spaced securement members, each of said members including an opening with a flared mouth to facilitate insertion of an arch wire, said mouth being narrowest at the junction of said mouth and said opening, the diameter of said arch wire being slightly larger than the width of the smallest opening of said mouth so that said arch wires snap into said opening when said arch wire is urged therein, said members each being deformable so that said mouth is closed by squeezing said member about said opening with a plier type tool to securely receive said arch wire at two spaced apart points and means for securing an insert bracket having a securement head, said head being disposed closer to the roots of said teeth to enable an arch wire to be secured to said teeth at one point per tooth.

3. The bracket of claim 1 wherein slotted means are in a line with said securement members to receive said arch wire.

4. The bracket of claim 3 wherein said slotted means includes a slot having a cross-section which is the same shape as said arch wire so that said arch wire is held snuggly in said slot.

5. The bracket of claim 1 and further including an auxiliary bracket having a slot which extends in the direction of and is aligned with the openings in said members.

6. An orthodontic bracket comprising a pair of spaced apart planar C-shaped arch wire securement members each having a portion of reduced thickness and an opening with a flared mouth and configured to enable snapping said arch wire into said opening, an intermediate member having a slot that extends in a direction which is aligned with the opening of said members, said intermediate member having a vertically extending channel for receipt of a bracket having an enlarged head which includes an opening with a flared mouth for securement of an arch wire therein.

7. The bracket of claim 6 wherein said intermediate member includes a pair of flanges which extend in opposed directions from said slot.

* * * * *